United States Patent [19]

Soucemarianadin et al.

[11] Patent Number: 5,302,878

[45] Date of Patent: Apr. 12, 1994

[54] HIGH-FREQUENCY ACOUSTIC RHEOMETER AND DEVICE TO MEASURE THE VISCOSITY OF A FLUID USING THIS RHEOMETER

[75] Inventors: Arthur Soucemarianadin, St. Peray; Renaud Gaglione, Valence; Pierre Attane, Grenoble, all of France

[73] Assignee: Imaje S.A., France

[21] Appl. No.: 969,338

[22] Filed: Oct. 30, 1992

[30] Foreign Application Priority Data

Oct. 30, 1991 [FR] France ............................ 91 13434

[51] Int. Cl.⁵ ...................... G01N 11/02; H01L 41/04; H01L 41/18
[52] U.S. Cl. .................................. 310/360; 310/333; 310/323; 73/54.27
[58] Field of Search ................. 73/54.24, 54.26, 54.27, 73/54.41, DIG. 4; 310/333, 334, 336, 360, 366, 369, 363, 364, 365, 323

[56] References Cited

U.S. PATENT DOCUMENTS

| | | | |
|---|---|---|---|
| 2,518,348 | 8/1950 | Mason | 310/369 |
| 2,707,391 | 5/1955 | McSkimin | 73/54.27 |
| 2,947,969 | 8/1960 | Harris | 310/369 |
| 3,719,907 | 3/1973 | Adler | 333/147 |
| 4,341,974 | 7/1982 | Calderara | 310/329 |
| 4,472,652 | 9/1984 | Brice et al. | 310/344 |
| 4,489,609 | 12/1984 | Burdess et al. | 310/366 |
| 4,652,786 | 3/1987 | Mishiro | 310/369 |
| 4,672,592 | 6/1987 | Skinner | 310/369 |
| 4,741,200 | 5/1988 | Hammerle | 310/312 |
| 4,799,378 | 1/1989 | Portman, Jr. et al. | 73/54 |
| 4,920,787 | 5/1990 | Dual et al. | 73/54.41 |

FOREIGN PATENT DOCUMENTS

0297032 12/1988 European Pat. Off. .
0112376 5/1991 Japan .................................. 310/333

OTHER PUBLICATIONS

World Patents Index, Sect. CH, Wk. 7749, Derwent Pubs., London & SU-A-403 294 (Shubnikov Crystallo) Apr. 27, 1977.
World Patents Index Latest, Sect. Ch, Wk. 9006, Derwent Pubs., London & JP-A-1 320 295, K. Fujutsu-C. Kinz, Dec. 26, 1989.
Journal of the Acoustical Society of America, vol. 90, No. 3, Sep.; 1991, N.Y., pp. 1287-1297, C. Barnes et al.

Primary Examiner—James C. Housel
Assistant Examiner—Theresa A. Trembley
Attorney, Agent, or Firm—Kerkam, Stowell, Kondracki & Clarke

[57] ABSTRACT

An acoustic rheometer working in the high frequency range comprises a torsional-mode transducer which is a crystal of the sillenites class, having a height that determines the resonance frequencies of the mode of torsion, and being provided with an electrical excitation means. Furthermore, the sensor is a rod made of an iron/nickel alloy having a very low thermoelastic coefficient. The rod is rigidly connected to the transducer. The respective diameters of the transducer and of the sensor are chosen so that the coefficient of reflection at the transducer/sensor interface is zero. The rheometer can be used in ink-based printing systems.

24 Claims, 4 Drawing Sheets

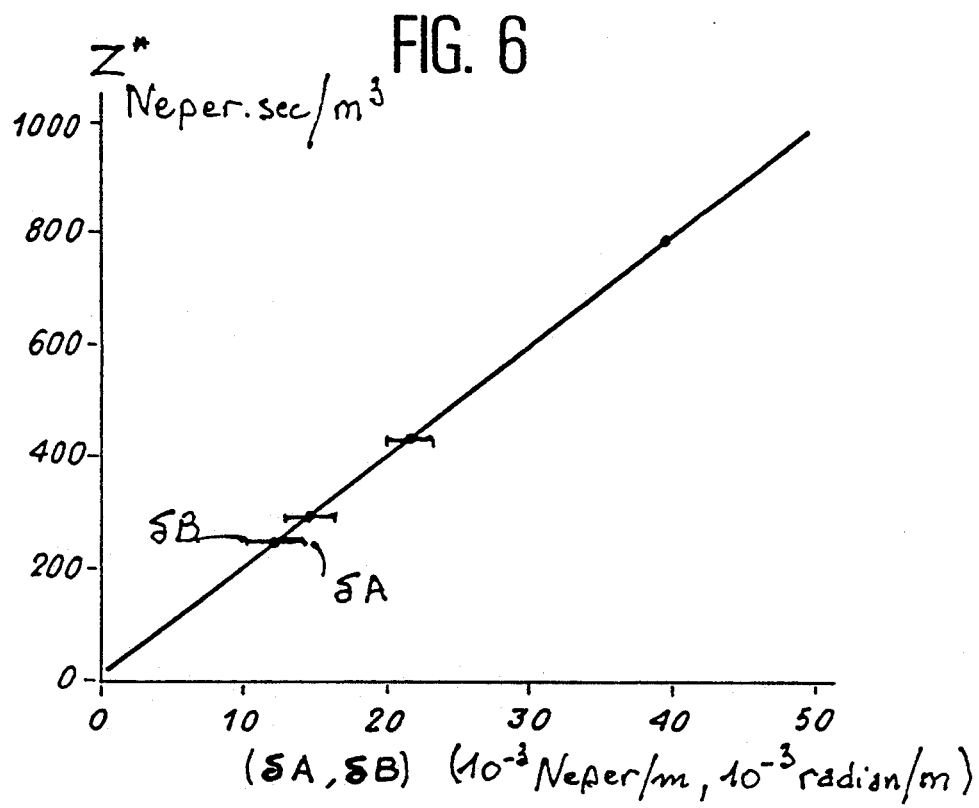
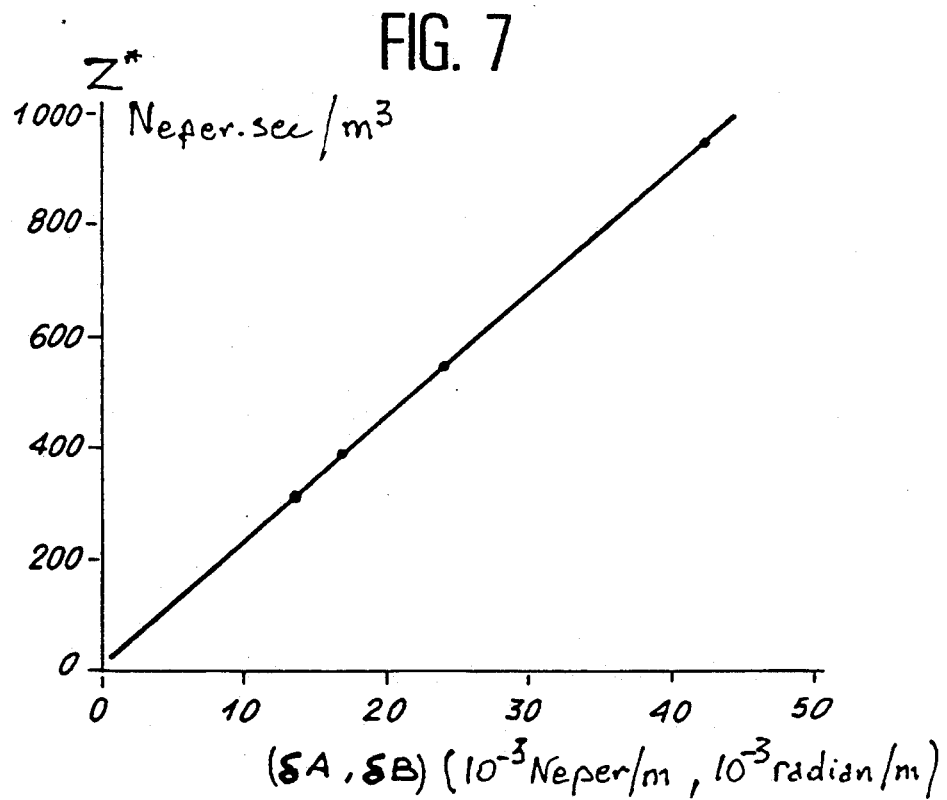

HIGH-FREQUENCY ACOUSTIC RHEOMETER AND DEVICE TO MEASURE THE VISCOSITY OF A FLUID USING THIS RHEOMETER

BACKGROUND OF THE INVENTION

The present invention relates to an acoustic rheometer enabling the measurement of the viscoelastic properties of a fluid subjected to periodic shear forces, and a device for the measuring of these properties through the use of the rheometer, notably in the high frequency range.

The value of high frequency measurements of viscosity and elasticity of fluids is that they provide access to the structure of these fluids in relation to their composition. The determining of the mechanical properties has major uses in industrial applications. Indeed these fluids come into play in numerous applications such as the manufacture of printing inks and paints, the agricultural processing industry, the lubrication of mechanical systems, or again the recovery of petroleum products.

In the especially promising application of the rheometer to the manufacturing of inks, since the frequency of the formation of the drops ranges from some tens of kilohertz to about 125 kilohertz, the rheometer should function in oscillating mode at a typical frequency of 100 kilohertz. To this end, the working of the rheometer is based on the following principle: the fluid to be studied is exposed to contact with a single moving surface, propelled to a torsional wave, which creates a simple shearing plane wave within this fluid, at a given frequency located in the 50 to 500 KHz range. The influence of the fluid on this shear wave, reflecting its viscoelastic properties, is measured by means of a variation in the characteristic impedance of the surface. The device used to measure these viscoelastic characteristics of the fluids, also called a rheometer, therefore comprises a transducer, generally made of a quartz crystal which is rigidly fixed to one end of a sensor. This sensor, which is made out of a cylindrical metal rod having the same diameter as the transducer, receives the vibrations from the quartz in the form of a wave train and its lateral surface in contact with the fluid creates a motion of shearing of the fluid. Two quantities characterize the propagation of these torsional waves in the rod: the phase speed B and the attenuation of amplitude A per unit of length. The reference state of the sensor is defined, in the absence of fluid, by a zero characteristic impedance $Z^*$ of the fluid, this state being non-dispersive. The propagation of the torsional waves that it receives is therefore characterized by a speed $B_o$ and an attenuation a that are inherent.

The presence of a fluid at the lateral interface of the sensor generates a variation of the attenuation of the amplitude $\delta A$ of the torsional wave as well as a variation of the phase speed $\delta B$ with respect to the reference state, these variations being proportional to the characteristic impedance $Z^*$ of the fluid. Indeed, the wave travels at a greater speed than in the reference state and leads to a phase-shift variation.

$$\delta B = B - B_o$$

Furthermore, the torsional wave with a pulsation is propagated by successive reflections on the lateral limit of the cylindrical sensor, each reflection being accompanied by a dissipation of the acoustic energy by the fluid. This prompts an increase in the attenuation A during the propagation of the wave:

$$\delta A = A - A_o$$

On the basis of the relationships of dispersal of the two states of the sensor and of the impedance $Z^*$, the basic formula that relates the cause to the effect:

$$Z^* = \frac{\alpha \cdot v \cdot a}{2} (\delta A + i\delta B)$$

is a linear relationship, where the constant of proportionality is a characteristic of the sensor, it being known that:

α is the mass in relation to the volume of the sensor,
v is the speed of propagation of the torsional wave in the rod, when there is no fluid,
a is the radius of the rod,
δA is the variation of phase-shift per unit of length, in nepers per meter,
δB is the variation of attenuation of amplitude per unit of length, in radians per meter.

As has been stated here above, the knowledge of the impedance $Z^*$ of the fluid gives access to the desired viscoelastic properties, for this impedance $Z^*$ is related by definition to the density $\alpha_1$ of the fluid which takes account of the inertia and to its complex viscosity $B^*$ by the following relationship:

$$Z^* = (i\Omega\alpha_1\beta^*)^{\frac{1}{2}}$$

$$Z = R + iX$$

So that the measurements of the variation of amplitude δA and of phase shift δB caused by the fluid in contact with the lateral surface of the cylindrical sensor make it possible to know the real part R and imaginary part X of the impedance $Z^*$ and to then obtain the complex viscosity $B^*$ of the fluid, given that:

$$\beta^* = \beta' - i\beta''$$

$$\beta' = 2RX/\Omega\alpha_1$$

$$\beta'' = (R^2 - X^2)/\Omega\alpha_1$$

The essential element of the high frequency rheometer is the torsional-mode transducer, generally constituted by piezoelectric quartz crystal in the shape of a cylinder, the torsional axis of which is parallel to one of its three second order crystallographic axes (the X axis), the quartz forming part of the class 32 of the triclinical system of the crystals. A torsional deformation is produced by exciting the crystal by an electrical signal by means of two pairs of electrodes oriented by $+/-45°$ with respect to the Y axis, perpendicularly to the X axis. Quartz possesses a very great stability of response in frequency so that the phase-shift introduced by the fluid can be measured with high precision.

However, a quartz rheometer such as this has a first drawback due to the fact that the electrically excited quartz generates a mode of torsion that is not pure but coupled to a radial vibration giving rise to a variation of the diameter of the crystal. This introduces a measurement error, probably due to the surface tension of the fluid, that exceeds the limits of precision hoped for from the stability in frequency. The error in measurement is all the greater as the fluid to be measured has low viscosity: imprecision of + or −15% is possible in the measurements.

A second drawback of a quartz rheometer arises out of the coupling coefficient of quartz, namely the output, in terms of mechanical energy, of the electrical stress applied to the quartz. This output is low, of the order of 3%, and makes it necessary to use excitation voltages of several hundreds of volts so that the sensor, which is coupled to the quartz crystal, receives an acoustic wave that is not greatly attenuated. The effect of the low coupling coefficient is to reduce the signal-to-noise ratio.

Other types of torsional-mode transducers are described in the French patent No. 2 327 677 and in the U.S. Pat. No. 3 719 907. In both these cases, the method used to make the torsional-mode transducer is lengthy, comprising several steps for the metallization of electrodes, polarization with intense electrical fields (several thousands of volts/mm) and selective etching. These different steps have the consequence of increasing the price of the transducer without any improvement, as compared with quartz transducers, in the performance characteristics relating to pure torsion deformation and high coupling coefficient.

Thus, in order to avoid these above-mentioned drawbacks with respect to the complexity of making the transducers, operation at a single frequency and imprecise measurements, above all at low viscosity, the aim of the present invention is the making of a high precision rheometer enabling the measurement of the viscoelastic characteristics of a large variety of liquids, in a wide range of temperatures and pressures. The rheometer according to the invention is furthermore provided with a transducer generating a pure torsion mode, with a high coupling coefficient, great reliability and simplicity of use, while at the same time permitting measurements at several resonance frequencies. This rheometer furthermore comprises a sensor that is is matched in impedance with the transducer and is stable in temperature.

SUMMARY OF THE INVENTION

According to another aim of the invention, the rheometer, which is automated by low-cost electronic instruments, is associated with a digital data processing system and can measure the viscosity of the fluids simultaneously with the density.

To this end, an object of the invention is an acoustic rheometer working in the high frequencies range, comprising a torsional-mode transducer formed by a piezoelectric crystal that emits and receives torsional waves, said crystal being electrically excited by means of electrodes, and being coupled to a sensor of said torsional waves that is plunged into a tube of fluid to be measured, the transducer and the sensor being placed in a chamber, wherein:

the transducer is a cylinder of a crystal belonging to the sillenites class, with a height determining the resonance frequencies of the mode of torsion, and provided with an electrical excitation means, the sensor is a rod made of an iron/nickel alloy that has undergone appropriate treatment and has a low thermoelastic coefficient; the sensor is connected rigidly to the transducer by means of a spot of bonder having a thickness far smaller than the wavelength of the torsional waves emitted by the transducer, the chamber is thermostat-controlled and constituted by a glass envelope, the internal wall of which constitutes the container of fluid which is kept at a constant pressure.

According to another characteristic of the invention, the transducer of the rheometer is either a crystal of bismuth and germanium oxide $Bi_{12}GeO_{20}$ or a crystal of bismuth and silicon oxide $Bi_{12}SiO_{20}$ or a crystal of bismuth and titanium oxide $Bi_{12}TiO_{20}$.

BRIEF DESCRIPTION OF THE DRAWINGS

Other advantages and characteristics of the invention shall appear from the following description of preferred embodiments, said description being made with reference to the appended drawings, of which:

FIG. 6 is the curve of sensitivity of a quartz rheometer for a Newtonian solvent and, FIG. 7 is the curve of sensitivity of a rheometer according to the invention for a Newtonian solvent.

In the different figures, the elements bearing the same references fulfil the same functions with a view to obtaining the same results.

DETAILED DESCRIPTION OF THE INVENTION

Figure 1:
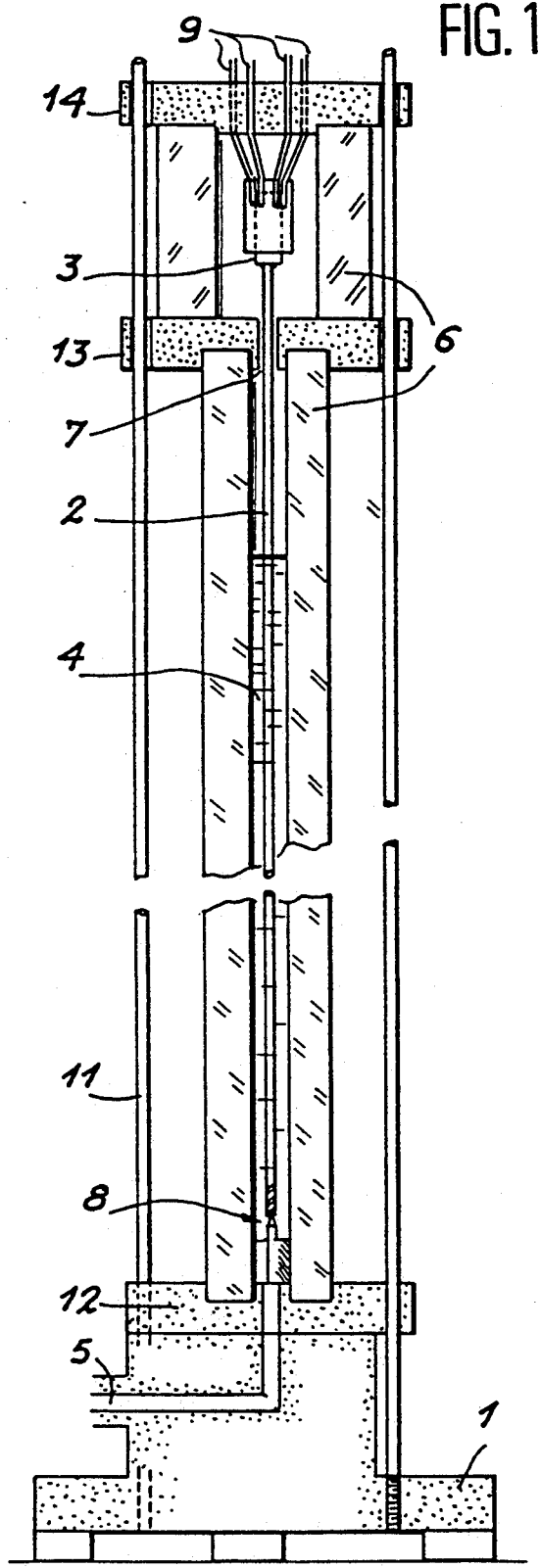
FIG. 1 is a drawing in longitudinal section illustrating a high frequency rheometer according to the invention.

FIG. 1 is a drawing in longitudinal section showing an exemplary embodiment of an acoustic rheometer according to the invention. The rheometer rests on a stand 1 made of a material that is dimensionally stable (such as steel for example) and essentially comprises two elements: the sensor 2, which is the site of the conversion of the mechanical impedance of the fluid to be tested into acoustic impedance, and the transducer 3, to which said sensor is fixed by bonding, designed to send out and receive the torsional wave.

The sensor 2 is a cylindrical metal rod made of an iron/nickel alloy, chosen notably for its very low expansion coefficient. Furthermore, the sensor made of iron/nickel alloy is inert with respect to organic solvents and withstands oxidation. Indeed, a temperature variation may by itself induce a phase-shift of the wave train by the combination of the heat expansion and of the variation of Coulomb's modulus of elasticity. A thermal annealing treatment of the rod enables the thermoelastic coefficient of torsion to be cancelled in order to obtain a variation of the dimensions of the sensor that is zero in the range of operating temperatures of the rheometer, and hence makes it possible to overcome the problems of thermostat control. The thermal cycle includes a rise in temperature up to the region of 350° C., then the maintaining of the temperature for several hours, and a slow cooling in an inert atmosphere in order to limit the oxidation. The rods are suspended vertically in the treatment furnace in order to prevent deformations, and a baking operation follows the heat treatment in order to set the thermoelastic properties of the rods. Thus, a stabilization to a precision within 0.1° C. is enough while the materials used in the prior art flow meters required thermal stabilization to a precision within 0.005° C.

Finally, the choice of the height of the rod is a function of the range of frequencies and of the speed of propagation of the torsional wave. The choice of the radius of the sensor takes account of the reference state of the rheometer for which the impedance is zero, the sensitivity of the rheometer which is inversely proportional to the radius and finally the connection between the sensor and the transducer which is set up by bonding. It is difficult to choose a radius of less than 2 mm, which corresponds to a cut-off frequency of over 1 MHz. This connection between the transducer 3 and the sensor 2 requires, for the sensor 2, great planeity of the upper face in contact with the transducer.

Furthermore, the state of the lateral surface of the sensor 2 should be of high quality owing to the distance of penetration of the shear wave in a fluid in contact with said sensor. This surface condition is trued by milling to obtain a very small arithmetical valley-to-peak height that is close to 0.12 $\mu$m, and the cylindricity of the rod is checked with the greatest possible precision.

The piezoelectric transducer 3 sends out a wave train that results from its vibration when it is subjected to the action of an external electrical field, but it also receives the moment of torsion after it has travelled in the sensor.

The transducer 3 is a crystal of the same class of symmetry as the sillenites, i.e. the class 23 of the cubic system and, especially, a crystal of bismuth and germanium oxide $Bi_{12}GeO_{20}$ or of bismuth and silicon oxide $Bi_{12}SiO_{20}$ or of bismuth and titanium oxide $Bi_{12}TiO_{20}$. The $Bi_{12}GeO_{20}$ crystal can be easily obtained in monocrystalline form by the Czochralski technique.

The crystal thus obtained is pale yellow with a density of 9.2 g/cm$^3$. It has highly piezoelectrical qualities, and is photoconductive and photorefractive. The basic material is machined from its crude form as obtained through crystal growth into cylinders of different lengths, which determine the resonance frequencies of the mode of torsion. It has low brittleness, can be easily machined and costs little.

The class 23 of symmetry of the cubic crystalline system has been chosen because it makes it possible to generate a motion of pure torsion with a high coefficient of electromagnetic coupling, indicating the ability of the piezoelectric crystal to convert the electrical energy into elastic energy or vice versa. For the oxide $Bi_{12}GeO_{20}$, the coupling coefficient is of the order of 32% for a plane plate.

The transducer 3 and the sensor 2 are rigidly connected to each other by a bonder joint which is the most satisfactory means of connection as regards acoustic transmission, for a bonder joint with a thickness 10 $\mu$m of represents less than 0.1% of the wavelength of the torsional wave, which is in the range of 1 cm to 100 KHz, and the measuring unit formed by the transducer and the sensor possesses an inherent attenuation.

The torsional wave undergoes an attenuation, firstly in a manner that is continuous with propagation in the sensor 2 and, secondly, in a localized way, by reflection at the ends of the sensor and at the interface between the transducer and the sensor. The losses related to propagation are due to the absorption and the diffusion of the wave, and are limited to below a frequency of 1 MHz.

As for the losses due to the reflection of the wave at the ends, they are negligible. Only the interface between the sensor and the transducer limits the transmission of the wave and fixes the level of the inherent attenuation of the system. The plane torsional wave continues to get propagated, in the region of the interface, in the reference mode for this region is not placed in contact with the fluid to be tested. The coefficient of reflection $A_r$ at the transducer-sensor interface, in making an approximation of two one-dimensional media, is written as:

$$A_r = \frac{Z_t D_t^4 - Z_c D_c^4}{Z_t D_t^4 + Z_c D_c^4}$$

where $Z_t$ and $Z_c$ are the respective acoustic impedances of the transducer and of the sensor and $D_t$ and $D_c$ are their respective diameters. Thus, the diameters $D_t$ and $D_c$ are chosen so as to cancel this reflection coefficient $A_r$.

The sensor 2 thus takes the form of a cylindrical rod with a length of about 700 mm. The perfectly plane upper face of this rod is bonded to the transducer and its lower face is drilled with a shallow conical aperture which houses a support tip 8 with a very small diameter (of 500 $\mu$m for example) enabling the sensor to be held vertically at the base while at the same time minimizing frictional motions, which minimizes frictional losses at reflection. This tip 8 is made of a material that is resistant to the different fluids to be tested with which it is in contact. In particular, their pH could be acid.

At the upper end, the sensor 2 is guided on a height of some millimeters by a vertical guiding element 7 which is a part having a shape generated by revolution, the diameter of which is very slightly greater than that of the sensor and the measuring unit, constituted by the sensor 2 and the transducer 3, is thermally insulated from the external environment by a thermostat-controlled double chamber 6. This chamber 6 is held vertically by three stay-rods 11 screwed, at the base, into the circular pedestal 1. Two disks 12 and 13 sliding in the stay-rods 11 enabling the horizontal setting. The thermostatically controlled chamber 6 of the sensor is constituted by a glass casing having the same height as the rod, and the chamber of the transducer 3 has a height that is about five times greater than the height of the transducer, these two chambers being fed in series with a heat-transfer fluid that keeps the temperature at a constant level.

The fluid to be tested is injected around the sensor 2, in the container constituted by the inner wall of the chamber 6, through an injection canal 5 placed in the lower disk 12, on a height smaller than that of the sensor 2. The diameter of the container should be far greater than that of the sensor 2 so that the wall of the container does play a part during the propagation of the torsional wave in the fluid. The upper disk 13 is drilled so as to maintain the pressure in the fluid container at a constant value equal to the atmospheric pressure.

Since the transducer 3 has to be subjected to the action of an electrical field in order to vibrate, electrical connections 9 supply voltage to electrodes placed against the transducer and emerge from the rheometer through a third sliding disk 14 which horizontally regulates the thermostat-controlled chamber of the transducer 3.

Figure 2:
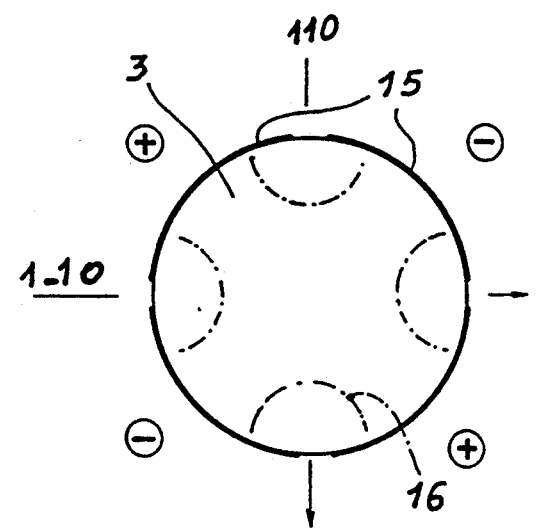
FIG. 2 is a cross-sectional view of a transducer according to the invention, provided with excitation electrodes arranged in dial form.

FIG. 2 is a cross-sectional view of the transducer according to the invention. The crystal is electrically excited by means of electrodes 15 arranged in a so-called dial configuration, i.e. each electrode covers a quarter of the lateral surface of the crystal 3 constituting the transducer. The electrodes are separated from one another by the crystallographic axes (110) and (1-10) and the electrodes, supplied with a positive voltage, alternate with those supplied with a negative voltage, thus creating field lines 16 in the form of arcs of circles.

To make these electrodes on the crystal, it is necessary, first of all, to determine the crystallographic orientation of the crystal by means of an X-ray goniometer, then deposit a thin layer of conductive metal by evaporation or sputtering for example. Then the metallized surface is divided by chemical etching to obtain the dial configuration.

The polarization device is constituted by four metal contactors, soldered vertically to a square support. The crystal of the transducer is capped by the device. The contactors exert slight pressure on the four lateral electrodes of the transducer, the points of contact being located at mid-height on the crystal. One advantage of this configuration of the electrodes lies in the obtaining of a high coupling coefficient (22%) for the fundamental mode.

Figure 3:
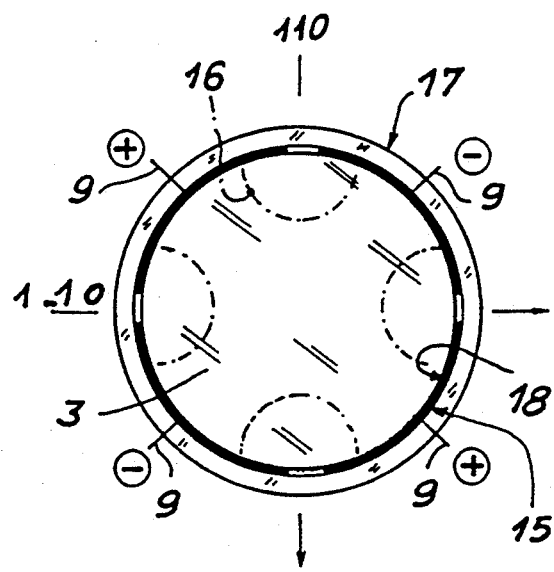
FIG. 3 is a cross-sectional view of a transducer according to the invention polarized by induction.

FIG. 3 shows a cross-section of the transducer according to the invention, polarized by influence, i.e. not bearing the electrodes directly on the crystal. It is capped by a glass tube 17 having the same height as the crystal but with a lower diameter that is slightly greater than that of the crystal. The glass tube is metallized on its internal face 18 facing the crystal, by laser evaporation for example.

The method consists in metallizing and etching the tube with a dial configuration designed to polarize the crystal of the transducer by electrostatic induction. The selected glass tube has perfectly controlled cylindricity and is metallized by the evaporation of chromium and nickel on its internal surface. The separation lines are made by thermal etching, using a laser ray focused on the internal surface of the tube. The diameter of the crystal cylinder forming the transducer should be finely adjusted to the internal diameter of the glass tube to minimize the interstice between the two lateral surfaces so as to limit the screen effect of the air.

Figure 4:
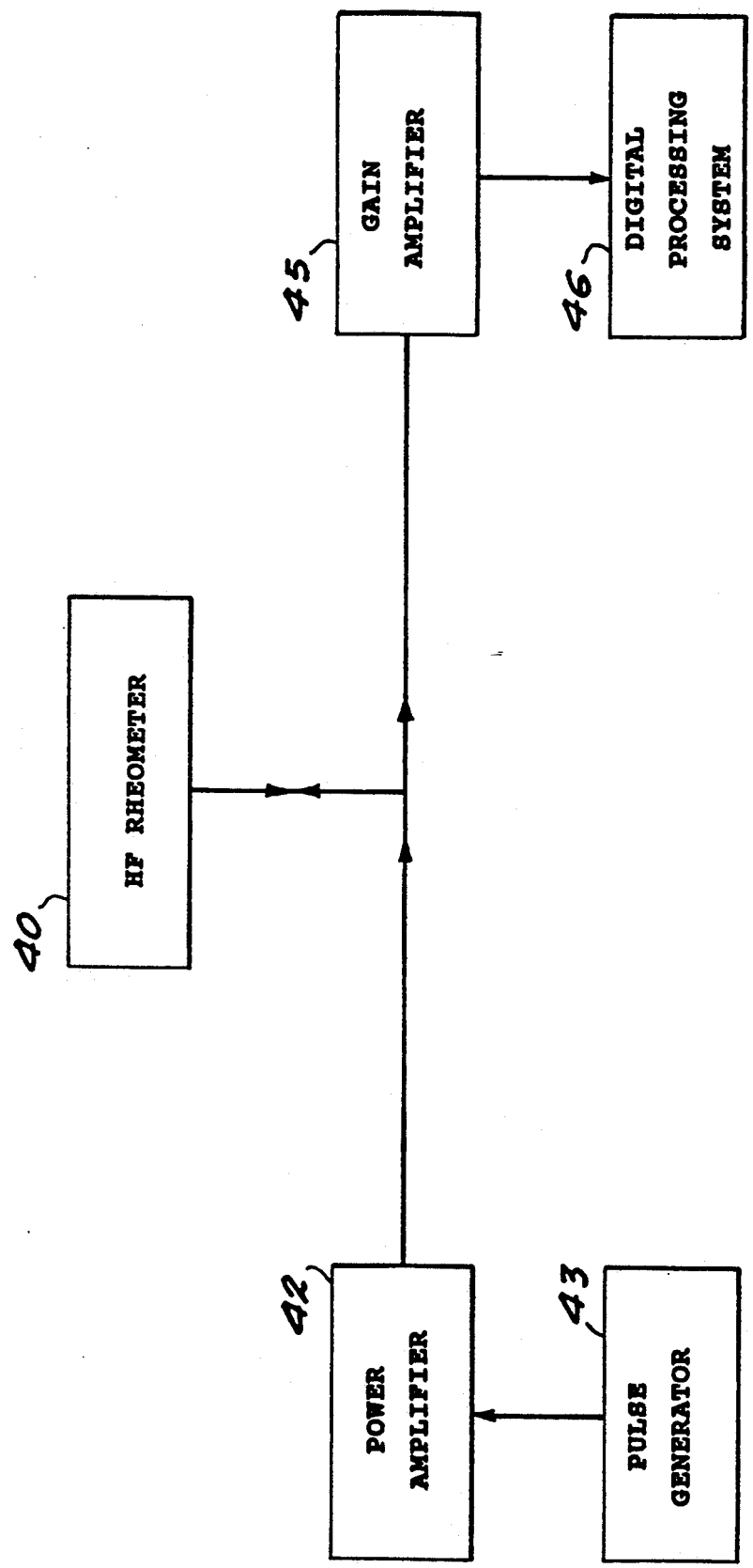
FIG. 4 is a diagram of the electronic system for the processing of the measurements performed by the rheometer according to the invention.

FIG. 4 is a diagram of the device for measuring the viscosity of a fluid, using a rheometer 40 which is an object of the invention.

It comprises, firstly, a pulse generator 41 that is connected to a power amplifier 42 in such a way that the signal coming from the pulse generator 41 is amplified before reaching the rheometer. It furthermore comprises a gain amplifier 45 which receives the output signal from the rheometer and is connected to a digital processing system 46 designed to measure the viscosity and the density of the fluid. The signal coming from the rheometer is hence amplified and then acquired and processed digitally.

The principle of operation of the rheometer is implemented by the pulse echoes method. During emission, an electrical signal is converted into a torsional impulse by the piezoelectric electrical transducer which receives it by means of the electrodes and gets propagated in the sensor up to its lower end where the torsional wave is reflected. This wave gets reflected in the reverse direction in the sensor and is then received by the transducer which reconverts it into an electrical signal: this is the first echo. By successive reflections at the two ends of the sensor, the initial pulse creates a series of M echoes.

Thus, the generator 41 emits a sinusoidal pulse, the carrier frequency of which is modulated in amplitude by a square pulse with a duration $\Gamma$. The pulse duration is chosen in such a way that two successive echoes get propagated in the sensor separately. For a sensor with a length of 700 mm, the transit time, of the order of 500 ms, sets a limit, which cannot be exceeded, of 50 periods for a pulse with a carrier frequency of 100 KHz. The frequency of emission of the pulse is 10 KHz. The time of 100 ms is greater than the duration of the inherent attenuation of the train of the echoes. The sensor is therefore crossed by only one series of echoes at a time. The signal delivered by the pulse generator is amplified by the power amplifier and sent to the transducer which then transmits the echos to the gain amplifier 45.

The rheometer makes it possible to measure the variations of attenuation of the amplitude $\Gamma A$ and of the phase-shift $\Gamma B$ of the wave, which are generated by the fluid in contact with the lateral surface of the sensor on a height h. Reduced to the unit of length, these variations are expressed as follows:

$$\delta A = \frac{\Gamma A}{2nh} \text{ and } \delta B = \frac{\Gamma B}{2nh}$$

The precision of the measurements therefore depends on the height h of the fluid in the rheometer and on the order n of the echo selected for the measurement. In the rheometer according to the invention, the impedance matching between the transducer and the sensor can be used to exploit the distant echos and hence to improve the precision.

The digital processing system 46 carries out first of all the sampling of the signals representing the echos and then the quantification on N levels of these very same signals. The precision of the measurements depends both on the levels of quantification and on the frequency of sampling. In the exemplary embodiment already mentioned, the number N of levels is equal to 8 and the frequency is equal to 500 points per period. Then, the processing system determines the variations $\delta A$ and $\delta B$ according to the following computations made within the permanent state of the echos and for different heights h of fluid in the container.

The initial sinusoidal pulse generates, in the reference state, i.e. without fluid, a series of echos:

$$U_n = U'_n \cos \Omega t,$$

varying from 1 to N

In the presence of fluid, the echo n acquires an attenuation of amplitude and an additional phase shift, and becomes:

$$u_n = U'_n e^{-\Gamma A} \cos(\Omega t - \Gamma B)$$

given that the dispersal of the wave train is negligible and that the transient state of the echos is not taken into account.

This electrical signal, which represents an echo, is acquired digitally by the processing system which takes the signal as a whole and not on a particular period of the wave train.

To determine the variation of attenuation of amplitude $\delta A$ per unit of length, first of all the variation $\delta A$ of the signal at the nth echo is considered:

$$u_n = U_n \cos(\Omega t - \Gamma B)$$

$$u_n = U'_n e^{-\Gamma A} \cos(\Omega t - \Gamma B)$$

whence $$\Gamma A = \log \frac{U'_n}{U_n} = 2nh\delta A$$

at the mth echo:

$$\Gamma A = \log \frac{U'_m}{U_m} = 2mh\delta A$$

In such a way that $\delta A$ $$\delta A = \frac{1}{2(n-m)h} \cdot \log \frac{U'_n}{U_n} \cdot \frac{U_m}{U'_m}$$

The acoustic power of the echo n integrates the signal on the duration of a period.

$$P_n = \frac{1}{T} \int_O^T g(\Omega) \cdot u_n^2(t) dt = g(\Omega) U_n^2$$

The electrical impedance $g(\Omega)$ depends on the frequency and the state of the sensor but not on the rank of the echo. The computation of the variation of the attenuation of amplitude $\delta A$ per unit of length is therefore obtained by the formula:

$$\delta A = \frac{1}{4(n-m)h} \cdot \log \frac{P'_n}{P_n} \times \frac{P_m}{P'_m}$$

To determine the variation of phase-shift $\delta B$, the signal is integrated with the duration of the emission and a computation is made of the product of the signal of an echo n in the reference state $u_n^0(t)$ and of the derivative of the signal of the same echo n in the presence of fluid $u_n(t)$. The result is equal to the area of the Lissajoux curve:

$$I_n = \int_O^T u'_n(t) \cdot \frac{du_n}{dt} dt$$

$$I_n = U'^2_n e^{-\Gamma A} \cdot \pi \cdot \sin \Gamma B$$

Furthermore, a computation is made of the product of the two signals of the same echo n:

$$Jn = \int_0^T u'_n(t) \cdot u_n(t) dt$$

The same operation is performed with a m order echo, distant from n.

Finally, the computation of the phase-shift variation is obtained by the formula:

$$\delta B = \frac{1}{2(n-m)h} \cdot \left( \text{Artan} \frac{I_n}{\Omega J_n} - \text{Artan} \frac{I_m}{\Omega J_m} \right)$$

in using two echos n and m.

As has been described here above, the determining of these variations $\delta A$ and $\delta B$ enables the computation of the characteristic impedance of the fluid and the deduction therefrom of its complex viscosity, its density being obtained by causing variation of the temperature of the fluid.

Figure 5A:
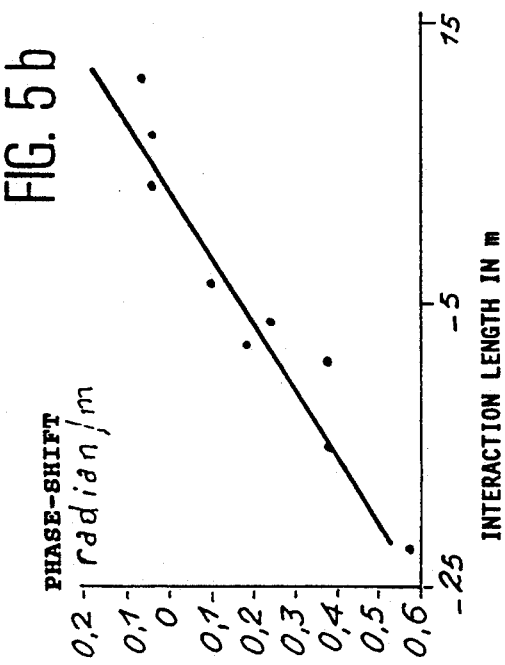
FIGS. 5a and 5b are curves of attenuation of amplitude and of phase-shifting of the torsional wave in a quartz rheometer, for alcohol.
Figure 5B:
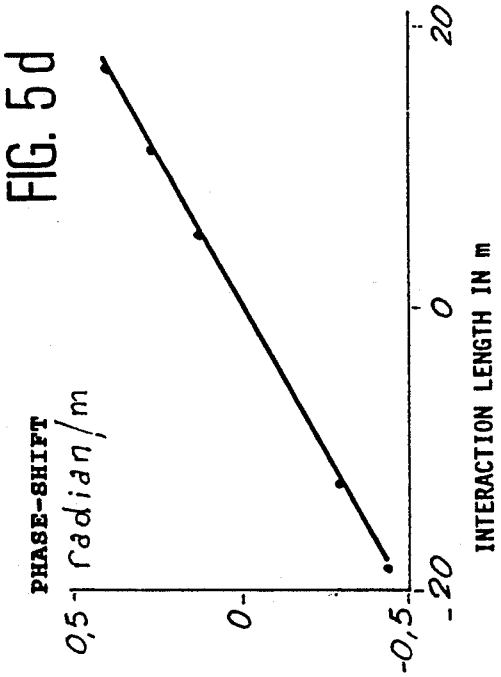
Figure 5C:
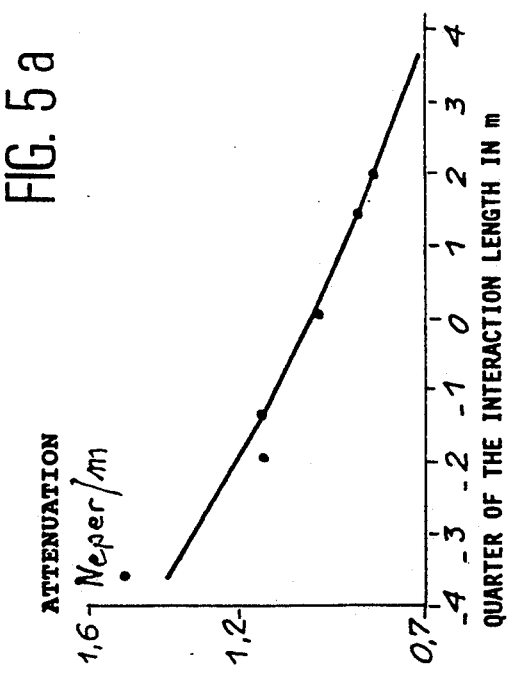
FIGS. 5c and 5d are the same curves for a rheometer according to the invention.
Figure 5D:
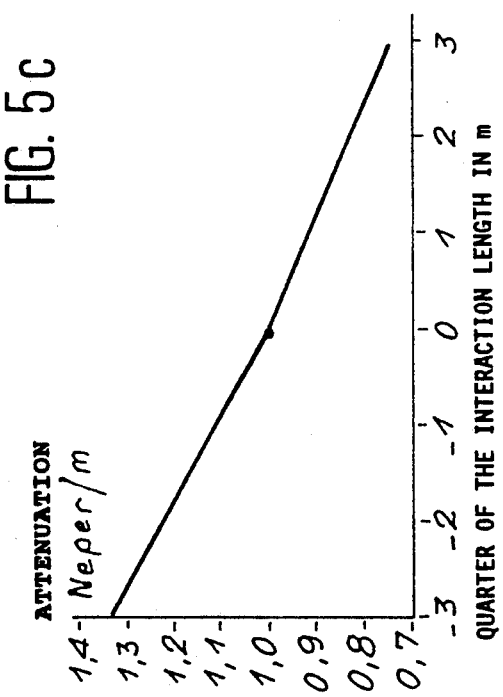

FIGS. 5a and 5b represent the curves of attenuation $\delta A$ and of phase-shift $\delta B$ of the torsional wave for alcohol, at 63 Khz, obtained for different heights of alcohol in the tube into which the sensor of the rheometer is plunged, in using a quartz rheometer. FIGS. 5c and 5d show the same curves for alcohol, with a bismuth and germanium oxide transducer $B_{12}GeO_{20}$. In comparing these curves, it is observed that is an error of nearly 5% with the quartz transducer whereas with $B_{12}GeO_{20}$, it is only 0.8%.

FIGS. 6 and 7 respectively show the curve of sensitivity of a rheometer with quartz transducer and a rheometer with a sillenites class crystal according to the invention, for Newtonian solvents. The curve of sensitivity is obtained by the plotting, on the X-axis, of the values of variation of attenation of amplitude $\delta A$ and of phase-shift measured by the rheometer, and on the Y-axis, of the value of the characteristic impedance $Z^*$ known by another method.

What is claimed is:

1. An acoustic rheometer comprising a torsional-mode transducer including a piezoelectric crystal electrically excited by means of electrodes, designed to emit and receive torsional waves, coupled to a sensor of said torsional waves plunged into a tube of fluid to be measured, said torsional-mode transducer and said sensor being placed in a thermostat-controllled chamber, maintained at constant pressure, wherein:

said torsional-mode transducer is a cylinder crystal belonging to the sillenites class, having a height determining the resonance frequencies of the torsional-mode, and being provided with an electrical excitation means, the sensor is a rod of an iron/nickel alloy having a low thermoelastic coefficient and connected rigidly to said torsional-mode transducer by means of a spot of bonder having a thickness far smaller than the wavelength of the torsional waves emitted by said torsional-mode transducer, the respective diameters of said torsional-mode transducer and of the sensor being such that the coefficient of reflection at the interface of the transducer/sensor is zero.

2. A rheometer according to claim 1, wherein the cylindrical crystal of said torsional-mode transducer is bismuth and germanium oxide $Bi_{12}GeO_{20}$.

3. A rheometer according to claim 2, wherein the means for the electrical excitation of the cylindrical crystal of said torsional-mode transducer is constituted by four electrodes arranged in a configuration of dials separated from one another by the crystallographic axes [110] and [1-10], each covering a quarter of the lateral surface of the cylindrical crystal, said four electrodes supplied with a positive voltage alternating with those supplied with a negative voltage, thus creating field lines in the shape of arcs of circles.

4. A rheometer according to claim 2, wherein the means for the electrical excitation of the cylindrical crystal of said torsional-mode transducer is constituted by a glass tube, the diameter of which is slightly greater than that of the crystal and is of the same height, surrounding said cylindrical crystal, said glass tube being metallized on its internal face facing the cylindrical crystal in such a way as to form at least two pairs of electrodes, alternately supplied with positive and negative voltages, for polarizing said torsional-mode transducer by induction.

5. A rheometer according to claim 2, wherein the height of the sensor is a function of range of operating frequencies of the rheometer and its radius is such that the impedance of the sensor is zero in the state of reference of the rheometer, without fluid.

6. A rheometer according to claim 2, wherein the chamber is thermostat-controlled and constituted by a glass casing, the internal wall of which constitutes the container of fluid, which is maintained at constant pressure.

7. A rheometer according to claim 1, wherein the cylindrical crystal of said torsional-mode transducer is bismuth and silicon oxide $Bi_{12}SiO_{20}$.

8. A rheometer according to claim 7, wherein the means for the electrical excitation of the cylindrical crystal of said torsional-mode transducer is constituted by four electrodes arranged in a configuration of dials separated from one another by the crystallographic axes [110] and [1-10], each covering a quarter of the lateral surface of the cylindrical crystal, said four electrodes supplied with a positive voltage alternating with those supplied with a negative voltage, thus creating field lines in the shape of arcs of circles.

9. A rheometer according to claim 7, wherein the means for the electrical excitation of the cylindrical crystal of said torsional-mode transducer is constituted by a glass tube, the diameter of which is slightly greater than that of the cylindrical crystal and is of the same height, surrounding said cylindrical crystal, said glass tube being metallized on its internal face facing the cylindrical crystal in such a way as to form at least two pairs of electrodes, alternately supplied with positive and negative voltages, for polarizing said torsional-mode transducer.

10. A rheometer according to claim 7, wherein the height of the sensor is a function of range of operating frequencies of the rheometer and its radius is such that the impedance of the sensor is zero in the state of reference of the rheometer, without fluid.

11. A rheometer according to claim 7, wherein the chamber is thermostat-controlled and constituted by a glass casing, the internal wall of which constitutes the container of fluid, which is maintained at constant pressure.

12. A rheometer according to claim 1, wherein the cylindrical crystal of said torsional-mode transducer is bismuth and titanium oxide $Bi_{12}TiO_{20}$.

13. A rheometer according to claim 12, wherein the means for the electrical excitation of the cylindrical crystal of said torsional-mode transducer is constituted by four electrodes arranged in a configuration of dials separated from one another by the crystallographic axes [110] and [1-10], each covering a quarter of the lateral surface of the cylindrical crystal, said four electrodes supplied with a positive voltage alternating with those supplied with a negative voltage, thus creating field lines in the shape of arcs of circles.

14. A rheometer according to claim 12, wherein the means for the electrical excitation of the cylindrical crystal of said torsional-mode transducer is constituted by a glass tube, the diameter of which is slightly greater than that of the cylindrical crystal and is of the same height, surrounding said cylindrical crystal, said glass tube being metallized on its internal face facing the cylindrical crystal in such a way as to form at least two pairs of electrodes, alternately supplied with positive and negative voltages, for polarizing said torsional-mode transducer.

15. A rheometer according to claim 12, wherein the height of the sensor is a function of range of operating frequencies of the rheometer and its radius is such that the impedance of the sensor is zero in the state of reference of the rheometer, without fluid.

16. A rheometer according to claim 12, wherein the chamber is thermostat-controlled and constituted by a glass casing, the internal wall of which constitutes the container of fluid, which is maintained at constant pressure.

17. A rheometer according to claim 1, wherein the means for the electrical excitation of the cylindrical crystal of said torsional-mode transducer is constituted by four electrodes arranged in a configuration of dials separated from one another by the crystallographic axes [110] and [1-10], each covering a quarter of the lateral surface of the cylindrical crystal, said four electrodes supplied with a positive voltage alternating with those supplied with a negative voltage, thus creating field lines in the shape of arcs of circles.

18. A rheometer according to claim 1, wherein the means for the electrical excitation of the cylindrical crystal of said torsional-mode transducer is constituted by a glass tube, the diameter of which is slightly greater than that of the cylindrical crystal and is of the same height, surrounding said cylindrical crystal, said glass tube being metallized on its internal face facing the cylindrical crystal in such a way as to form at least two pairs of electrodes, alternately supplied with positive and negative voltages, for polarizing said torsional-mode transducer by induction.

19. A rheometer according to claim 1, wherein the height of the sensor is a function of range of operating frequencies of the rheometer and its radius is such that the impedance of the sensor is zero in the state of reference of the rheometer, without fluid.

20. A rheometer according to claim 19, wherein the chamber undergoes a thermal annealing treatment to cancel the thermoplastic coefficient of torsion, in the range of temperatures of operation of the rheometer.

21. A rheometer according to claim 1, wherein the chamber is thermostat-controlled and constituted by a glass casing, the internal wall of which constitutes the container of fluid, which is maintained at constant pressure.

22. A device to measure the viscosity of a fluid using a rheometer, comprising an acoustic rheometer comprising a torsional-mode transducer including a piezoelectric crystal electrically excited by means of electrodes, designed to emit and receive torsional waves, coupled to a sensor of said torsional waves plunged into a tube of fluid to be measured, the torsional-mode transducer and the sensor being placed in a chamber, wherein:

said transducer is a cylinder of crystal belonging to the sillenites class, having a height determining the resonance frequencies of the torsional-mode, and being provided with an electrical excitation means, the sensor is a rod of an iron/nickel alloy having a low thermoelastic coefficient and connected rigidly to said transducer by means of a spot of bonder having a thickness far smaller than the wavelength of the torsional wave emitted by the transducer, the respective diameters of the transducer and of the sensor being such that the coefficient of reflection at the interface of the transducer/sensor is zero, said acoustic rheometer working at emission and at reception according to the method of pulse echoes, said device comprising an electrical pulse generator followed by a power amplifier which is connected to the rheometer, said rheometer being connected furthermore to a gain amplifier that is followed by a digital processing means for measuring the viscosity of the fluid.

23. A measuring device according to claim 22, wherein the digital processing means is constructed and arranged to carry out the following steps for several heights of fluid in the tube of the rheometer:

sampling of the signals representing the pulse echoes;

quantifying, on N levels, of said signals;

determining of the variation of attenuation of the amplitude ($\delta A$) of the torsional wave, per unit of length, for at least two distinct and distant n order and m order echoes, and then in the permanent state of the pulse echoes;

determining of the variation of phase-shift ($\delta B$) of the torsional wave, per unit of length, for the measurements of n order and m order echoes;

determining of the characteristic impedance of the fluid from the measurements of ($\delta A$) and ($\delta B$);

computation of the complex viscosity of the fluid, from the characteristic impedance; and computation of the density of the fluid by causing variation in the operating temperature of the rheometer.

24. A measuring device according to claim 23, wherein the determining of the variation of attenuation of the amplitude ($\delta A$), is obtained, for the n order and m order pulse echoes, by the following steps:

the computation of the acoustic power ($P_n$) and ($P_m$) of the n order and m order pulse echoes respectively;

the computation of the Napierian logarithm of the ratio of the acoustic power values of said pulse echoes respectively in the reference state of the rheometer ($P'_n$ and $P'_m$) and in the presence of fluid ($P_n$ and $P_m$), equal to twice the variation of attenuation of the wave ($\Gamma A$) at the n order and m order echoes:

$$\Gamma A = \frac{1}{2} \log \frac{P_n'}{P_n}$$

computation of the variation of attenuation ($\delta A$) per unit of length by the application of the formula:

$$\delta A = \frac{1}{4(n-m)h} \cdot \log \frac{P_n'}{P_n} \times \frac{P_m}{P_m'}$$

and wherein the determining of the variation of phase-shift ($\delta B$) of the torsional wave is obtained by the following steps for each of the n and m order echoes:

computation of the integral, on a period (T) of emission of the wave, of the product of the signal representing the echo in the reference state of the rheometer u'(t) and of the derivative with respect to the time of the signal of the same pulse echo u(t) in the presence of the fluid:

$$I_n = U'_n{}^2 e^{-\Gamma A} \cdot \pi \sin \Gamma B$$

and $$I_m = U'_m{}^2 e^{-\Gamma A} \cdot \pi \sin \Gamma B$$

computation of the integral, on a period (T), of the product of the two signals u'(t) and u(t):

$$J_n = \int_0^T u_n'(t) \cdot u_n(t) dt \text{ and}$$

$$J_m = \int_0^t u_m'(t) \cdot u_m(t) dt$$

computation of variation of phase-shift ($\delta B$) from the integrals $I_n$, $I_m$, $J_n$ and $J_m$ by the formula:

$$\delta B = \frac{1}{4(n-m)h} \left[ \arctan \frac{I_n}{\Omega J_n} - \arctan \frac{I_m}{\Omega J_m} \right].$$

* * * * *

UNITED STATES PATENT AND TRADEMARK OFFICE
CERTIFICATE OF CORRECTION

PATENT NO. : 5,302,878
DATED : April 12, 1994
INVENTOR(S) : SOUCEMARIANADIN et al It is certified that error appears in the above-indentified patent and that said Letters Patent is hereby corrected as shown below:

Col. 12, line 43 (Claim 20, line 2) "chamber" should be --sensor--.

Col. 14, line 24 (2nd formula) "Pn'" should be "P'n".

Col. 14, line 24 (2nd formula) "Pm'" should be "P'm".

Signed and Sealed this

Twenty-ninth Day of November, 1994

Attest:

BRUCE LEHMAN

*Attesting Officer*    *Commissioner of Patents and Trademarks*